(12) United States Patent
Smadi et al.

(10) Patent No.: US 6,703,033 B2
(45) Date of Patent: Mar. 9, 2004

(54) ADVANCES IN TOWELETTES CONTAINING ORGANIC CARBONATES

(75) Inventors: Raeda M. Smadi, Round Rock, TX (US); James R. Machac, Jr., Lago Vista, TX (US); Edward T. Marquis, Austin, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 09/842,451

(22) Filed: Apr. 26, 2001

(65) Prior Publication Data

US 2002/0192267 A1 Dec. 19, 2002

(51) Int. Cl.$^7$ ................................................ A01N 25/34
(52) U.S. Cl. ...................... 424/402; 424/409; 424/413; 424/64; 424/443; 510/405; 510/108; 510/118; 510/130
(58) Field of Search ................................. 424/402, 409, 424/413, 443, 64; 510/405, 108, 118, 130

(56) References Cited

U.S. PATENT DOCUMENTS

| 4,801,331 A | * | 1/1989 | Murase ........................... 106/5 |
| 5,043,155 A | | 8/1991 | Puchalski et al. .............. 424/78 |
| 5,173,288 A | * | 12/1992 | Everhart et al. ............... 424/61 |
| 5,207,838 A | | 5/1993 | Googin et al. ................. 134/42 |
| 5,540,332 A | | 7/1996 | Kopacz et al. ............... 206/494 |
| 5,618,522 A | | 4/1997 | Kaleta et al. .................. 424/60 |
| 5,648,083 A | | 7/1997 | Blieszner et al. ............ 424/402 |
| 5,691,289 A | * | 11/1997 | Purcell et al. ............... 510/174 |
| 5,965,115 A | | 10/1999 | Bolich, Jr. et al. ........ 424/70.12 |
| 6,106,820 A | | 8/2000 | Morrissey et al. ........ 424/78.18 |
| 6,139,827 A | | 10/2000 | Cohen et al. ............. 424/70.16 |
| 6,156,711 A | * | 12/2000 | Perlman ...................... 510/118 |

FOREIGN PATENT DOCUMENTS

JP          08059437 A2  *  3/1996

* cited by examiner

*Primary Examiner*—Thurman K. Page
*Assistant Examiner*—Lakshmi Channavajjala
(74) *Attorney, Agent, or Firm*—Russ R. Stolle; Ron D. Brown; Christopher J. Whewell

(57) ABSTRACT

Provided herein are moist towelettes useful for cleansing, among other things, hard surfaces and human skin. The moist towelettes of the invention comprise a towelette portion which is moistened with a liquid composition of matter wherein the liquid composition includes an alkylene carbonate as one of its components. According to one preferred form of the invention, the liquid composition from which the towelettes are made moist are alcohol-free. In another embodiment, a substantial portion of the alcohol in a given formulation is replaced with an alkylene carbonate component. Preferred alkylene carbonate components include propylene carbonate, butylene carbonate, and glycerine carbonate.

31 Claims, No Drawings

ADVANCES IN TOWELETTES CONTAINING ORGANIC CARBONATES

This invention relates to compositions of matter useful for cleansing a wide range of surfaces and substrates, including hard surfaces such as walls, countertops, motorized vehicles, ovens, stoves, floors, etc. The compositions are also useful in cleaning human skin and in a preferred embodiment, the compositions according to the invention are applied to a surface that is desired to be cleansed by means of a towelette that is nearly saturated with a composition of the invention.

BACKGROUND

The use of moist towelettes for cleaning surfaces has been known for some time and the prior art is replete with moist towelette products designed for cleaning a wide range of surfaces. Certain towelettes are known in the prior art to be useful for cleaning walls, countertops, motorized vehicles, ovens, stoves, floors, etc., in addition to human skin. One well-known and popular variant of moist towelettes are those which are used on cleaning infants during the changing of diapers. Such towelettes are typically dispensed from a sealed container having a slit or other narrow opening through which the end piece of a continuous roll or interfolded stack of towelette stock that has been pre-moistened with a cleaning composition is disposed, to enable the consumer to tear off or grasp a single towelette for immediate use while simultaneously causing the next towelette in the continuous roll or interfolded stack to be advanced through the opening or slit for ready grasping when another towelette is needed. Many such products and dispensers for same are available in the marketplace, including: "Swifter", "Charmin Kid Fresh", and "Mr. Klean Wipe-Ups", available from Procter & Gamble; "Clorox Disinfecting Wipes" available from The Clorox Company; "Pledge Grab-It" available from SC Johnson & Sons; and "Huggies" available from Kimberly-Clark Corporation, to name but a few.

These and other prior art moist towelettes generally suffer from several disadvantages, one being that in many cases alcohols are used as part of the formulations which the towelettes are pre-moistened. The drawback of using alcohols in such formulations is that when a towelette containing an alcohol is contacted with the skin, some of the alcohol remains on the skin of the person contacted. In some cases, a degree of dehydration of the skin results. In other cases, the cooling caused by the evaporation of the alcohol creates an uncomfortable chill sensation, particularly in the case of infants. In yet other cases where such wipes are used around the peribulbar region and other facial areas, alcohol vapors emitted by the towelette can cause temporary eye irritation. In addition, alcohols are undesirable from the standpoint of their flammability. Thus, if the presence of alcohols could be avoided in towelettes designed for human skin contact, such would be desirable. Yet the solvency characteristics of alcohols in general render them as desirable components for use in towelettes. Thus, owing to the balance between the favorable and unfavorable characteristics of moist towelettes containing alcohol-bearing compositions, alcohols are often deemed to be an indispensable component for towelettes used in some applications. However, if a suitable substitute non-alcoholic material were discovered having substantially the equivalent level of solvency characteristics associated with alcohols in such a use, and if such substitute had a relatively low vapor pressure, was benign to human skin, and was non-flammable, then alternate formulations for moist towelette compositions could be provided. The present invention provides such formulations.

SUMMARY OF THE INVENTION

The present invention is concerned with towelettes for use in applications in which human skin contact occurs with the towelette. According to the present invention, in the case of towelettes which contain a cleaning composition which includes an alcohol, the present invention is concerned with replacement of all or a substantial portion of the alcohol with an alkylene carbonate. In the case of towelettes which contain a cleaning composition which does not include an alcohol, the cleaning composition benefits further by addition of alkylene carbonate to the formula.

DETAILED DESCRIPTION

The present invention is concerned with moist towelettes suitable for many uses including among other uses cleaning hard surfaces, and cleansing human skin. The compositions used to soak, impregnate, saturate, or moisten moist towelettes have historically contained a surfactant component, water, various alcohols, fragrances, preservatives, organic acids and other components. Of these components, alcohols are preferably included because of their solvency and cleaning characteristics. However, the use of alcohols is generally undesirable because of their cost, volatility and offensive nature. Further, alcohols cause a cooling effect on skin because of their enthalpy of vaporization, which in the cases where moist towelettes which contain an alcohol component are contacted with the skin of an infant, create a momentary cold shock on the infant.

The liquid compositions used in making moist towelettes according to the present invention are compositions in which all or a portion of the alcohol component of a prior art moist towelette is replaced with an alkylene carbonate. Stated another way, the liquid compositions for making moist towelettes according to the invention comprise an alkylene carbonate, in combination with other components contained in conventional moist towelettes, with the exception of the presence of alcohols, which is minimized or totally eliminated. In those cases of prior art formulations for which moist towelettes which contain no alcohol, the present invention is concerned with adding an alkylene carbonate to the composition(s) with which such towelettes are made wet, to enhance their performance in wiping applications. Thus, liquid compositions used in making moist towelettes according to the present invention comprise an alkylene carbonate. It is preferred that an alkylene carbonate is present in a composition according to the invention in an amount effective to provide a moist towelette made moist using such composition as having solvency characteristics equal to or better than a towelette made moist using pure isopropanol with respect to cleaning a test soil prepared in accordance with testing procedure ASTM D-4488, section A6.4.3 from a substrate of vinyl tile as described below.

Cleaning Performance

The cleaning performance of the liquid compositions of the present invention was determined by comparing the optical reflectance of white vinyl tiles treated with an exemplary test soil before and after cleaning with the solution. The test soil is one which is prepared in accordance with testing procedure ASTM D-4488, section A6.4.3, by adding the following ingredients in the indicated order and then mixing for 30 minutes:

TABLE 1

Soil Preparation ASTM (D-4488)

| Ingredient | Grams |
|---|---|
| Paint Thinner | 50 |
| Vegetable oil | 4 |
| Mineral oil | 10 |
| Clay | 10 |
| Carbon Black | 4.5 |

In practice of the testing, the soil composition was applied to vinyl tiles by paintbrush, and the soiled tiles were then heat treated at 60° C. for one hour. Three vinyl tiles for each sample were cleaned with The tiles were then rinsed with water containing 150 ppm hardness. Cleaning efficiency was determined from reflectance readings obtained from a Hunter "LABSCAN XE" Color Quest Reflectometer which were taken before soiling, after soiling, and after cleaning. Soil removal was calculated as a percentage using the following formula:

$$SR\% = (R_w - R_s)/(R_0 - R_s) * 100$$

where $R_w$ = Reflectance of tiles after cleaning;

$R_s$ = Reflectance of tiles before cleaning; and $R_0$ = Reflectance of tiles before soiling.

In addition, other materials may be present in such compositions(s), including glycols and glycol ethers, or other alkylene carbonates.

The alcohols suitable as components of a composition used in making a moist towelette according to the invention include without limitation: methanol, ethanol, n-propanol, isopropanol. However, all alcohols recognized by those skilled in the art as providing a benefit to cleaning compositions are suitable as components of liquid compositions from which moist towelettes may be made according to the present invention.

The glycols suitable as components of a composition used in making a moist towelette according to the invention include without limitation: propylene glycol; dipropylene glycol; polypropylene glycol having a molecular weight between 134 and 2000; butylene glycol; dibutylene glycol; polybutylene glycol having a molecular weight between 162 and 2000; and glycerol. However, all glycols recognized by those skilled in the art as providing a benefit to cleaning compositions are suitable as components of liquid compositions from which moist towelettes may be made according to the present invention.

The glycol ethers suitable as components of a composition used in making a moist towelette according to the invention include, without limitation: propylene glycol methyl ether; dipropylene glycol methyl ether; propylene glycol butyl ether; dipropylene glycol butyl ether; butylene glycol methyl ether; and butylene glycol butyl ether. However, all glycol ethers recognized by those skilled in the art as providing a benefit to cleaning compositions are suitable as components of liquid compositions from which moist towelettes may be made according to the present invention.

The alkylene carbonates suitable as components of a composition used in making a moist towelette according to the invention include, without limitation: ethylene carbonate ("EC"), propylene carbonate ("PC"), butylene carbonate ("BC"), and glycerine carbonate ("GC").

The surfactants suitable as components of a composition used in making a moist towelette according to the invention includes cationic surfactants, zwitterionic surfactants, amphoteric surfactants, anionic surfactants, and non-ionic surfactants. The most preferred surfactants for use in the invention are: alkyl and alkenyl sulfates having between 10 and 18 carbon atoms per molecule; alkyl and alkenyl ethoxylated sulfates having any number of moles of ethylene oxide per molecule between 1 and 9; succinamates; fatty acid esters; isethionic acid; alkylamino sulfonates, alkylbetaines, alkyl amido betaines, quaternary ammonium salts, alkyl phenol alkoxylates, and alcohol alkoxylates.

However, all surfactants recognized by those skilled in the art as capable of providing a benefit to cleaning compositions are suitable as components of liquid compositions from which moist towelettes may be made according to the present invention.

Following are exemplary formulations which may be used in providing a moist towelette according to the invention. All quantities of materials are specified in percentages by weight based upon the total weight of the composition. Materials having the SURFONIC® trademark are available from Huntsman Petrochemical Corporation, 7114 North Lamar Boulevard, Austin, Tex. To provide a moist towelette according to the invention, one begins with a piece of fabric, which may be, without limitation a non-woven or woven fabric of any material composition (including cellulosics and polymeric fiber-based materials) which is capable of absorbing a liquid composition, and contacting the liquid composition with the fabric until the fabric becomes moist to the touch by virtue of its having absorbed some of the liquid composition. This may be done by immersion, spraying, or any other process for wetting a cloth surface with a liquid substance known to those skilled in the art.

Example 1

| | |
|---|---|
| Propylene carbonate | 9 |
| Surfonic ® CO-42 | 4 |
| PPG-1-PEG-9 Lauryl glycol ether | 3 |
| PPG-2-methyl ether | 1 |
| Fragrance | 1.2 |
| BHT | 0.5 |
| Phenoxyethanol | 0.16 |
| Methyldibromo glutaronitrile | 0.04 |
| Aloe barbadensis gel | 0.01 |
| Water | 75.09 |

Example 2

| | |
|---|---|
| Ethanol | 2 |
| Propylene carbonate | 18 |
| Propylene glycol monomethyl ether | 2 |
| Surfonic ® N-SB4SS | 0.06 |
| Fragrance | 0.02 |
| Water | 77.92 |

Example 3

| | |
|---|---|
| Propylene carbonate | 9.0 |
| Propylene glycol | 4.0 |
| PEG-75 | 1.5 |
| Lanolin | 1.00 |
| Disodium cocoamphodiacetate | 0.40 |
| Polysorbate 20 | 3.00 |
| Methylparaben | 0.10 |
| Propyleparaben | 0.10 |
| 2-bromo-2-nitropropane-1,3-diol | 0.03 |
| fragrance | 0.02 |
| water | 80.85 |

Example 4

| | |
|---|---|
| Ethanol | 8 |
| Propylene carbonate | 12 |
| Propylene glycol monomethyl ether | 2 |

-continued

| | |
|---|---|
| Surfonic ® N-SB4SS | 0.06 |
| Fragrance | 0.02 |
| Water | 77.92 |

Example 5

| | |
|---|---|
| isopropanol | 8 |
| alkylene carbonate-any of PC, BC, or GC, or combinations thereof totaling: | 12 |
| Propylene glycol monomethyl ether | 2 |
| Surfonic ® N-SB4SS | 0.06 |
| Fragrance | 0.02 |
| Water | 77.92 |

Example 6

| | |
|---|---|
| Propylene glycol | 2.5 |
| Propylene carbonate | 1.0 |
| methylparaben | 0.30 |
| propylparaben | 0.04 |
| ethoxylated sorbitol | 0.4 |
| fatty acid ester (surfactant) | 1.0 |
| water | 95.76 |

Example 7

| | |
|---|---|
| dipropylene glycol monobutyl ether | 1.5 |
| Propylene carbonate | 1.0 |
| methylparaben | 0.30 |
| propylparaben | 0.04 |
| ethoxylated sorbitol | 0.4 |
| fatty acid ester (surfactant) | 1.0 |
| water | 95.76 |

Example 8

| | |
|---|---|
| dibutylene glycol monomethyl ether | 1.5 |
| glycerine carbonate | 1.0 |
| methylparaben | 0.30 |
| propylparaben | 0.04 |
| ethoxylated sorbitol | 0.4 |
| fatty acid ester (surfactant) | 1.0 |
| water | 95.76 |

Example 9

| | |
|---|---|
| diethylene glycol | 1.0 |
| glycerine carbonate | 3.0 |
| methylparaben | 0.30 |
| propylparaben | 0.04 |
| ethoxylated sorbitol | 0.4 |
| fatty acid ester (surfactant) | 1.0 |
| water | 95.76 |

Example 10

| | |
|---|---|
| Isopropanol | 8 |
| glycerine carbonate | 12 |
| Propylene glycol monomethyl ether | 2 |
| Surfonic ® N-SB4SS | 0.06 |
| Fragrance | 0.02 |
| Water | 77.92 |

One particular advantage of the inclusion of an alkylene carbonate as a component in an alcohol-free formulation from which moist towelettes are provided according to the present invention is that the moist towelettes may be caused to have a vapor pressure that is less than or equal to the vapor pressure of water. Of course this is only true when no components having a vapor pressure greater than that of water, such as alcohols, are present in the liquid formulation used to make the towelettes moist. According to a preferred embodiment of the invention, moist towelettes have a vapor pressure that is less than or equal to water. However, in other preferred embodiments, the vapor pressure of the towelettes have a vapor pressure which is only slightly elevated over that of water, as in cases where there is an alcohol such as isopropyl alcohol present in an amount of less than about 10% by weight of the total weight of the composition used to make the towelettes moist.

TABLE II vapor pressures of various alkylene carbonates and water.

| Material | Temperature | Vapor Pressure (mmHg) |
|---|---|---|
| Ethylene Carbonate | 20 | 0.0217 |
| | 25 | 0.0340 |
| | 30 | 0.0522 |
| | 35 | 0.0788 |
| | 40 | 0.1171 |
| Propylene Carbonate | 20 | 0.023 |
| | 25 | 0.0371 |
| | 30 | 0.0584 |
| | 35 | 0.0901 |
| | 40 | 0.1365 |
| Butylene Carbonate | 20 | 0.0180 |
| | 25 | 0.0285 |
| | 30 | 0.0445 |
| | 35 | 0.0680 |
| | 40 | 0.1021 |
| Glycerine Carbonate | 20 | 0.0000 |
| | 25 | 0.0000 |
| | 30 | 0.0000 |
| | 35 | 0.0000 |
| | 40 | 0.0001 |
| water | 20 | 17.40 |
| | 25 | 23.63 |
| | 30 | 31.71 |
| | 35 | 42.08 |
| | 40 | 55.26 |

One of the advantages of a moist towelette according to the invention is that they may be caused to have a vapor pressure which is only slightly greater than, or no greater than, a moist towelette made moist with water itself. This is advantageous in providing a moist towelette having the cleaning power of an alcohol soaked towelette when no alcohol is present, which alcohol of present would tend to puff out any sealed packaging containing such alcohol-bearing towelettes, which problem is familiar to those skilled in the art. Further, the towelettes according to the invention have literally no odor in those cases when they are alcohol-free.

In table III below are shown comparative physical properties results of cleaning performance of a towelette according to the invention which is moistened in one case with a solution containing 10% isopropyl alcohol and no propylene carbonate, and in the other case with a solution containing 5% propylene carbonate and 5% isopropyl alcohol. The soil removal % was conducted as described earlier herein, and the streaking test is evaluated by visual observation using a scale of 1–5, in which a rating of "1" is the best and a rating of "5" is the worst. From the data in this table it can be seen that as the isopropyl alcohol component is removed and replaced with propylene carbonate, the vapor pressure of the towelette is beneficially decreased, while the streaking performance and soil removal is enhanced.

TABLE III comparative performance properties of hard surface cleaning formulations containing propylene carbonate and those containing no propylene carbonate

| Hard Surface Cleaner Formulae | #1 | #2 | Windex ® |
|---|---|---|---|
| | wt. % | wt. % | — |
| Isopropyl Alcohol | 5 | 10 | — |
| Propylene Carbonate | 5 | 0 | — |

TABLE III-continued comparative performance properties of hard surface cleaning formulations containing propylene carbonate and those containing no propylene carbonate

| Hard Surface Cleaner Formulae | #1 | #2 | Windex ® |
|---|---|---|---|
| Propylene Glycol Monomethyl Ether | 2 | 2 | — |
| Surfonic ® N-SB4SS | 0.05 | 0.05 | — |
| Fragrance | 0.02 | 0.02 | — |
| Water | 87.93 | 87.93 | — |
| Soil Removal % | 96.59 | 96.25 | 68.25 |
| Streaking | 1 | 2 | 2 |
| Vapor Pressure (mmHg @ 50° C.) | 120 | 135 | |

Thus, owing to the various combined beneficial properties conferred upon moist towelettes by the formulations herein described, it is anticipated that moist towelettes containing propylene carbonate according to the invention shall be of great benefit to the general public.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

We claim:

1. A moist towelette made from a material selected from the group consisting of: non-woven fabrics and cellulosic materials, wherein said towelette is moistened with a liquid composition of matter which comprises:
   I) an organic compounds component including:
      a) an organic carbonate; and
      b) a surfactant,
         wherein said organic carbonate is present in the highest amount of any and all organic compounds which are present in said liquid composition; and
   II) an inorganic component including:
      a) water.

2. A towelette according to claim 1 wherein said organic compounds component further comprises: c) an alcohol.

3. A towelette according to claim 2 wherein said alcohol is selected from the group consisting of: methanol, ethanol, n-propanol, isopropanol.

4. A towelette according to claim 1 wherein said organic compounds component further comprises a glycol.

5. A towelette according to claim 2 wherein said organic compounds component further comprises a glycol.

6. A towelette according to claim 4 wherein said glycol is selected from the group consisting of: propylene glycol; dipropylene glycol; polypropylene glycol having a molecular weight between 134 and 2000; butylene glycol; dibutylene glycol; polybutylene glycol having a molecular weight between 162 and 2000; and glycerol.

7. A towelette according to claim 5 wherein said glycol is selected from the group consisting of: propylene glycol; dipropylene glycol; polypropylene glycol having a molecular weight between 134 and 2000; butylene glycol; dibutylene glycol; polybutylene glycol having a molecular weight between 162 and 2000; and glycerol.

8. A towelette according to claim 1 wherein said organic compounds component further comprises a glycol ether.

9. A towelette according to claim 2 wherein said organic compounds component further comprises a glycol ether.

10. A towelette according to claim 8 wherein said glycol ether is selected from the group consisting of: propylene glycol methyl ether; dipropylene glycol methyl ether; propylene glycol butyl ether; dipropylene glycol butyl other; butylene glycol methyl ether; and butylene glycol butyl ether.

11. A towelette according to claim 9 wherein said glycol ether is selected from the group consisting of: propylene glycol methyl ether; dipropylene glycol methyl ether; propylene glycol butyl ether; dipropylene glycol butyl ether; butylene glycol methyl ether; and butylene glycol butyl ether.

12. A towelette according to claim 1 wherein said organic carbonate is selected from the group consisting of: propylene carbonate, butylene carbonate, and glycerine carbonate.

13. A towelette according to claim 1 wherein said surfactant is a surfactant selected from the group consisting of: alkylbenzene sulfonate surfactants, quaternary ammonium surfactants, and alkoxylated alcohol surfactants.

14. A towelette made from a material selected from the group consisting of: non-woven fabrics and cellulosic materials, wherein said towelette is moistened with a liquid composition of matter which comprises:
   I) an organic compounds component including:
      a) an organic carbonate; and
      b) a surfactant,
         wherein said organic carbonate is present in an amount of at least 50% by weight based upon the total weight of any and all organic compounds present in said liquid composition; and
   II) an inorganic component including:
      a) water.

15. A towelette according to claim 14 wherein said organic compounds component further comprises: c) an alcohol.

16. A towelette according to claim 15 wherein said alcohol is selected from the group consisting of: methanol, ethanol, n-propanol, isopropanol.

17. A towelette according to claim 14 wherein said organic compounds component further comprises a glycol.

18. A towelette according to claim 15 wherein said organic compounds component further comprises a glycol.

19. A towelette according to claim 17 wherein said glycol is selected from the group consisting of: propylene glycol; dipropylene glycol; polypropylene glycol having a molecular weight between 134 and 600; butylene glycol; dibutylene glycol; polybutylene glycol having a molecular weight between 162 and 600; and glycerol.

20. A towelette according to claim 18 wherein said glycol is selected from the group consisting of: propylene glycol; dipropylene glycol; polypropylene glycol having a molecular weight between 134 and 600; butylene glycol; dibutylene glycol; polybutylene glycol having a molecular weight between 162 and 600; and glycerol.

21. A towelette according to claim 14 wherein said organic compounds component further comprises a glycol ether.

22. A towelette according to claim 15 wherein said organic compounds component further comprises a glycol ether.

23. A towelette according to claim 21 wherein said glycol ether is selected from the group consisting of: propylene glycol methyl ether; dipropylene glycol methyl ether; propylene glycol butyl ether; dipropylene glycol butyl ether; butylene glycol methyl ether; and butylene glycol butyl ether.

24. A towelette according to claim 22 wherein said glycol ether is selected from the group consisting of: propylene glycol methyl ether; dipropylene glycol methyl ether; propylene glycol butyl ether; dipropylene glycol butyl ether; butylene glycol methyl ether; and butylene glycol butyl ether.

25. A towelette according to claim 14 wherein said organic carbonate is selected from the group consisting of: ethylene carbonate, propylene carbonate, butylene carbonate, and glycerine carbonate.

26. A towelette according to claim 14 wherein said surfactant is a surfactant selected from the group consisting of: alkylbenzene sulfonate surfactants, quaternary ammonium surfactants, and alkoxylated alcohol surfactants.

27. A moist towelette made from a material selected from the group consisting of: non-woven fabrics and cellulosic materials, wherein said towelette is moistened with a liquid composition of matter which comprises:
   I) an organic compounds component including:
      a) an organic carbonate; and
      b) a surfactant,
         wherein said organic carbonate is present in the highest amount of any and all organic compounds present in said liquid composition; and
   II) an inorganic component including:
      a) water,
wherein said liquid component contains no material having a vapor pressure at 25° C. that is greater than water.

28. A moist towelette made from a material selected from the group consisting of: non-woven fabrics and cellulosic materials, wherein said towelette is moistened with a liquid composition of matter which comprises:
   I) an organic compounds component including:
      a) an organic carbonate; and
      b) a surfactant,
wherein said organic carbonate is present in the highest amount of any and all organic compounds present in said liquid composition; and
   II) an inorganic component including water,
wherein said moist towelette has a vapor pressure of less than 120 mm Hg at 50° centigrade.

29. A moist towelette according to claim 28 having a vapor pressure of less than 40 mm Hg at 25° centigrade.

30. A moist towelette according to claim 28 having a vapor pressure of less than 30 mm Hg at 25° centigrade.

31. A moist towelette according to claim 28 further comprising an alcohol component present in said organic compounds component, wherein the total amount of alcohol is less than 10% by weight of the liquid composition.

* * * * *